United States Patent [19]

Kang

[11] Patent Number: 5,080,835
[45] Date of Patent: Jan. 14, 1992

[54] POLYMETALATED 1-ALKYNE COMPOSITIONS

[75] Inventor: Jung W. Kang, Clinton, Ohio

[73] Assignee: Bridgestone/Firestone, Inc., Akron, Ohio

[21] Appl. No.: 586,489

[22] Filed: Sep. 21, 1990

[51] Int. Cl.$^5$ .............................................. C07F 1/02
[52] U.S. Cl. ................ 260/665 R; 502/152; 502/157
[58] Field of Search ............... 260/665 R; 502/152, 502/157

[56] References Cited

U.S. PATENT DOCUMENTS

| | | | |
|---|---|---|---|
| 3,135,716 | 6/1964 | Uranek et al. | 260/45.5 |
| 3,159,587 | 12/1964 | Uranek et al. | 252/431 |
| 3,193,590 | 7/1965 | Hsieh | 260/665 |
| 3,296,150 | 1/1967 | Kahle | 252/431 |
| 3,303,225 | 2/1967 | Hseih et al. | 260/665 |
| 3,377,404 | 4/1968 | Zelinski | 260/680 |
| 3,438,957 | 4/1969 | Hsieh | 260/94.1 |
| 3,644,322 | 2/1972 | Farrar | 260/94.2 |
| 3,668,263 | 6/1972 | Morrison et al. | 260/665 R |
| 3,725,368 | 4/1973 | Morrison et al. | 260/84.7 |
| 3,784,637 | 1/1974 | Farrar | 260/448.2 Q |
| 3,787,510 | 1/1974 | Farrar | 260/665 R |
| 3,903,168 | 9/1975 | Foss et al. | 260/583 R |
| 3,975,453 | 8/1976 | Smith, Jr. | 260/665 R |
| 4,075,253 | 2/1978 | Harüe et al. | 260/665 R |
| 4,196,154 | 4/1980 | Tung et al. | 260/665 R |
| 4,339,397 | 7/1982 | Ishihara et al. | 260/665 R |
| 4,399,078 | 8/1983 | Morrison | 260/665 R |
| 4,497,748 | 2/1985 | Vitus et al. | 260/665 R |
| 4,822,530 | 4/1989 | Bronstert et al. | 260/665 R |

OTHER PUBLICATIONS

Eberly and Adams in J. Organometal. Chem., 3 (1965), 165-167.
H. E. Adams et al, in Kautschuk and Gummi, Kunststoffe 18, Jahrgang, pp. 709-716, Nr. 11-1965.
Makowski et al., J. Macromol. Sci.-Chem., E2(4), pp. 683-700, Jul., 1968.
Masuda et al, Macromolecules, vol. 20, No. 7, (1987), pp. 1467-1487.

*Primary Examiner*—Arthur C. Prescott
*Attorney, Agent, or Firm*—Daniel N. Hall

[57] ABSTRACT

Hydrocarbon soluble polymetalated 1-alkene compositions are described, and these compositions may be characterized by the formula

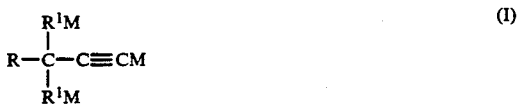

(I)

wherein R is hydrogen, a hydrocarbyl group or $R^1M$, M is an alkali metal, $R^1$ is a divalent oligomeric hydrocarbyl group comprising moieties derived from a conjugated diene, and wherein the total number moieties derived from a conjugated diene in all of the $R^1$ groups in Formula I is from about 2 to about 30. Preferably, the alkali metal is lithium.

Hydrocarbon soluble polymetalated 1-alkene catalysts for anionic polymerizations are also described which comprise the reaction product of a 1-alkyne, an organometallic compound $R°M$, and a 1,3-conjugated diene wherein $R°$ is a hydrocarbyl group, M is an alkali metal, the mole ratio of conjugated diene to 1-alkyne is at least about 2:1, and the reaction is conducted at a temperature of at least about 70° C.

37 Claims, No Drawings

POLYMETALATED 1-ALKYNE COMPOSITIONS

TECHNICAL FIELD OF THE INVENTION

This invention relates to novel polymetalated 1-alkyne compositions. More particularly, this invention relates to such compositions containing two, three or four alkali metal substituents per molecule. The compositions are useful as catalysts in anionic polymerizations.

BACKGROUND OF THE INVENTION

Various alkali metal acetylides have been described in the literature, and various procedures for preparing such acetylides have been suggested. U.S. Pat. No. 3,303,225 describes a procedure for preparing alkali metal acetylides containing more than one alkali metal atom per molecule. In particular, the polymetalated acetylenes are prepared by reacting an organoalkali metal compound with an acetylene under conditions to effect step-wise replacement of, first, the acetylenic hydrogen atom and, second, the hydrogen atoms attached to the carbon atom which is alpha to the acetylenic linkage. The patentees indicate that the metalated 1-acetylenes are active as polymerization initiators for vinylidene-containing monomers.

The metalation of 1-butyne with excess n-butyllithium is discussed by Eberly and Adams in *J. Organometal. Chem.*, 3(1965) 165-167. The authors report that two moles of n-butyllithium react with one mole of 1-butyne to yield a hexane-insoluble 3-methylpropynylene-1,3-dilithium. Three moles of n-butyllithium are reported to react with one mole of 1-butyne to yield a hexane-insoluble 3-methylpropynylenedilithium n-butyllithium adduct.

The stereopolymerization of butadiene and styrene in the presence of acetylenes and ketones is described by H. E. Adams et al, in *Kautschuk und Gummi. Kunststoffe* 18. Jahrgang, pp. 709-716, Nr, 11/1965. The authors studied the reaction of 1-butyne with 1, 2 and 3 moles of n-butyllithium in hexane, and the use of the materials obtained from such reactions as catalysts. The reaction of 1-butyne with one mole of n-butyllithium resulted in the formation of a white precipitate where the acetylenic hydrogen was replaced by lithium. When a second mole of n-butyllithium was added slowly to the reaction mixture, the white precipitate dissolves and the product is a clear lemon-yellow solution. Upon standing at room temperature, the solution becomes cloudy, and after about 210 hours, the precipitation of a yellow solid is complete. The product was identified as 1,3-dilithio-1-butyne. When an excess of n-butyllithium is added to the precipitate of 1,3-dilithio-1-butyne, the precipitate dissolves to form a golden-yellow solution. There were signs of precipitation after two weeks, and after two months, a copius precipitate had formed. The precipitate is identified as a complex of 1,3-dilithio-1-butyne and n-butyllithium.

The use of dilithium salts in the polymerization of butadiene is reported by Makowski et al, *J. Macromol. Sci.—Chem.*, E2(4) pp. 683-700, July, 1968. Among the lithium compounds studied were the 1,3-dilithioacetylides such as the compounds obtained by reacting 1-hexyne with n-butyllithium in ratios of 0.5 and 0.67. At a ratio of 0.5, homogeneous catalyst solutions in hydrocarbons were obtained. Above this ratio, some precipitate was present. In all cases, however, polymerization with butadiene resulted in low molecular weight polymer solutions. That is, where the catalyst solution included precipitated solids, the solids dissolved during the course of the polymerization. At the ratio of 0.5, the polymer solution was very viscous, and at the ratio of 0.67 a gelled solution resulted. However, when Attapulgus clay was added to the viscous solution or to the gelled solution, fluid solutions were obtained. This result was attributed to the presence of water in the clay.

Masuda et al, *Macromolecules*, Vol. 20, No. 7, (1987) pp 1467-1487 describe the preparation of poly[3-(trimethylsily)-1-alkynes]. The monomeric 3-(trimethylsilyl)-1-alkynes are prepared by reacting a 1-alkyne with n-butyllithium to prepare the 1,3-dilithiated intermediate which is then reacted with chlorotrimethylsilane to form the desired monomer.

Polylithium polymerization initiators also are described in U.S. Pat. No. 3,377,404. The initiators are prepared by first contacting an excess of lithium with an organic halide containing two to four halogen atoms in a polar solvent such as ether. The intermediate formed in the this step can be represented by the formula $$RLi_x$$

wherein x is an integer of two to four and R is a hydrocarbon group. In a second step, the intermediate is contacted with a small amount of a conjugated diene such as 1,3-butadiene. The amount of diene is generally from about one to about ten moles per mole of lithium compound. After the intermediate has been treated in this manner, a substantial portion or all of the polar solvent is removed and replaced by a hydrocarbon diluent. The polylithiated hydrocarbon soluble compounds prepared in this manner are reported to be useful as initiators of the polymerization of conjugated dienes.

U.S. Pat. No. 3,784,637 describes multi-functional polymerization initiators prepared from polyvinylsilane compounds or polyvinylphosphine compounds. More particularly, the multi-functional polymerization initiators are prepared by reacting an organomonolithium compound such as n-butyllithium with a polyvinyl phosphine compound or polyvinylsilane compound. Preferably, the reaction is conducted in the presence of a solublizing monomer such as a polymerizeable conjugated diene, monovinyl-substituted aromatic compound, or mixtures thereof. Examples of solublizing monomers include conjugated dienes such as 1,3-butadiene and aromatic vinyl compounds such as styrene.

SUMMARY OF THE INVENTION

Hydrocarbon soluble polymetalated 1-alkyne compositions are described, and in one embodiment, these compositions may be characterized by the formula

wherein R is hydrogen, a hydrocarbyl group or R$^1$M, M is an alkali metal, R$^1$ is a divalent oligomeric hydrocarbyl group comprising moieties derived from a conjugated diene, and wherein the total number moieties derived from a conjugated diene in all of the R$^1$ groups in Formula I is from about 2 to about 30. Preferably, the alkali metal is lithium.

In another embodiment, the invention relates to hydrocarbon soluble polymetalated 1-alkyne catalyst for anionic polymerizations comprising the reaction product of a 1-alkyne, an organometallic compount R°M, and a 1,3-conjugated diene wherein R° is a hydrocarbyl group, M is an alkali metal, the mole ratio of conjugated diene to 1-alkyne is at least about 2:1, and the reaction is conducted at a temperature of at least about 70° C.

DESCRIPTION OF THE PREFERRED EMBODIMENTS

Polymetalated 1-alkyne compositions of one embodiment of the present invention are characterized by the formula

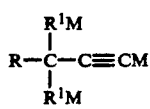

wherein R is hydrogen, a hydrocarbyl group or $R^1M$, M is an alkali metal, $R^1$ is a divalent oligomeric hydrocarbyl group comprising moieties derived from a conjugated diene, and wherein the total number moieties derived from a 1,3-conjugated diene in all of the $R^1$ groups in Formula I is from about 2 to about 30.

As noted, R may be hydrogen or a hydrocarbyl group which may be a saturated aliphatic, saturated cycloaliphatic or an aromatic group generally containing up to about 20 carbon atoms. In one embodiment, R is an alkyl group containing from 1 to 15 carbon atoms. In another embodiment, R is an alkyl group containing 1 to 6 carbon atoms. In a further embodiment R is an alkyl group containing from 3 to about 9 carbon atoms. M is an alkali metal including lithium, sodium, potassium, rubidium, cesium and francium. Lithium, sodium and potassium are preferred alkali metals, and lithium is the most preferred alkali metal, particularly when the polymetalated compositions of the present invention are to be used as polymerization catalysts.

The substituent $R^1$ is a divalent oligomeric hydrocarbyl group comprising moieties derived from a 1,3-conjugated diene. The conjugated dienes may be any of a variety of 1,3-conjugated dienes including those containing from four to 12 carbon atoms, and preferably from four to eight carbon atoms per molecule. Specific examples of the conjugated dienes include: 1,3-butadiene; isoprene; 2,3-dimethyl-1,3-butadiene; 1,3-pentadiene(piperylene); 2-methyl-3-ethyl-1,3-butadiene; 3-methyl-1,3-pentadiene; 1,3-hexadiene; 2-methyl-1,3-hexadiene; 1,3-heptadiene; 1,3-octadiene; etc. In one preferred embodiment, the moeties of the oligomeric group $R^1$ are derived from 1,3-butadiene, isoprene or piperylene.

The number of moieties derived from a conjugated diene in the $R^1$ groups of the composition of Formula I may be varied over a range of from two to about 30. Generally, the total number of moieties derived from a conjugated diene in all of the $R^1$ groups in the composition of Formula I is from about three to about 30. In one preferred embodiment, the total number of conjugated diene derived moieties in all of the $R^1$ groups in the composition of Formula I is from about eight to about 20. The number of moieties derived from a conjugated diene in the oligomeric groups $R^1$ can be varied to provide compositions of Formula I having a weight average molecular weight of from about 200 to about 3000. In one preferred embodiment, the weight average molecular weight of the compositions of Formula I is within a range of from about 800 to about 2000.

The hydrocarbon soluble tri- and tetrametalated 1-alkyne compositions characterized by Formula I and additional hydrocarbon soluble polymetalated 1-alkyne compositions of other embodiments of the present invention can be obtained by reacting a 1-alkyne, an organometallic compound R°M, and a conjugated diene at a temperature above about 70° C. The 1-alkyne may be represented by the formula

wherein R and $R^3$ are each independently hydrogen or a hydrocarbyl group. Representative examples of such 1-alkyne compounds include 1-propyne; 1-butyne; 1-pentyne; 1-hexyne; 1-octyne; 1-decyne, 1-dodecyne; 1-hexadecyne; 1-octadecyne; 3-methyl-1-butyne; 3-methyl-1-pentyne; 3-ethyl-1-pentyne; 3-propyl-6-methyl-1-heptyne; 3-cyclopentyl-1-propyne; etc.

The organometallic compound may be represented by the formula R°M wherein R° is a hydrocarbyl group which may be a saturated aliphatic group, a saturated cycloaliphatic group, or an aromatic group. Generally, R° will contain up to about 20 carbon atoms. M is an alkali metal including lithium, sodium, potassium, rubidium, cesium and francium. Representative examples of the organometallic compound R°M include: methylsodium, ethyllithium; propyllithium; isopropylpotassium, n-butyllithium, s-butyllithium; t-butylpotassium; t-butyllithium; pentyllithium; n-amylrubidium; tert-octylcesium; phenyllithium; naphthyllithium; etc. The conjugated dienes which are reacted with the intermediate to form the desired compositions are preferrably 1,3-conjugated dienes of the type which have been described above.

In a preferred embodiment, the polymetalated 1-alkyne compositions of the present invention are prepared by the method which comprises the steps of (a) reacting a 1-alkyne with an organometallic compound R°M to form an intermediate, and (b) reacting said intermediate with a conjugated diene at a temperature of at least about 70° C. The mole ratio of R°M to 1-alkyne is between about 2:1 and about 4:1. The mole ratio of conjugated diene to 1-alkyne in the reaction is at least about 2:1 and may be as high as about 30:1. More generally, the ratio will be in the range of from about 8:1 to 20:1.

The reaction of the 1-alkyne with the organometallic compound followed by reaction with the conjugated diene can be carried out in the presence of an inert diluent, and particularly, in the presence of a hydrocarbon such as an aliphatic, cycloaliphatic or aromatic hydrocarbon. Representative examples of suitable hydrocarbon diluents include n-butane, n-hexane, isooctane, decane, dodecane, cyclohexane, methylcyclohexane, benzene, toluene, xylene, etc. Preferred hydrocarbons are aliphatic hydrocarbons containing from four to about 10 carbon atoms per molecule. Mixtures of hydrocarbons can also be utilized.

The number of metal substituents introduced into the compositions of the present invention will depend primarily upon the type of 1-alkyne, and the relative amounts of the 1-alkyne and the organometallic compounds present in the initial reaction to form the intermediate. In order to obtain at least one metal substituent on the carbon atom which is alpha to the alkyne group, more than one mole of the organometallic compound must be reacted with one mole of the 1-alkyne since the first hydrogen to be displaced by the metal is the hydrogen attached to the acetylenic group. Accordingly, the compositions of the present invention generally will be obtained by reacting at least about two moles of an organometallic compound with each mole of the 1-alkyne. When the 1-alkyne contains two hydrogens attached to the carbon atom adjacent to the triple bond (a methylene carbon), a molar ratio of organometallic compound to 1-alkyne of 2:1 results in the formation of a dimetal compound, and the use of a molar ratio of 3:1 results in a trimetalated compound. For example, the reaction of one mole of propyne with one mole of n-butyllithium will form 1-lithiopropyne; two moles of n-butyllithium will form 1,3-dilithiopropyne; three moles of n-butyllithium will form 1,3,3-trilithiopropyne; and four moles of n-butyllithium will form 1,3,3,3-tetralithiopropyne. The reaction between one mole of 1-butyne and one mole of n-butyllithium results in the formation of 1-lithio-1-butyne; the reaction of one mole of 1-butyne with two moles of n-butyllithium results in the formation of 1,3-dilithio-1-butyne; and the reaction of one mole of 1-butyne with three moles of n-butyllithium at a temperature in excess of about 70° C. results in the formation of 1,3,3-trilithio-1-butyne. Larger amounts of the organometallic compound can be utilized, but such larger amounts are usually unnecessary. The reaction between the 1-alkyne and the organometallic compound to form the intermediate can be effected in temperatures of 20°-30° C., and the reaction is generally conducted in an inert atmosphere such as under nitrogen. The reaction generally is conducted at atmospheric pressure. The intermediate obtained from the first step is a polymetalated alkyne which is either insoluble or only slightly soluble in hydrocarbons.

The reaction between the intermediate and the conjugated diene to form a hydrocarbon soluble product is conducted at a temperature above 70° C. and more generally at a temperature of from about 70° C. to about 150° C. The reaction generally is completed in less than about 5 hours, and the reaction results in a change in the color of the solution from a yellow to red or reddish brown. At about 80° C. the reaction is completed in about 3 hours. At higher temperatures, the reaction is completed in less than 3 hours. If the reaction mixture is heated for too long a period, the catalytic activity of the resulting product may be reduced. The product of this reaction is a polymetalated alkyne containing one or more divalent oligomeric hydrocarbyl groups comprising moieties derived from the conjugated diene. Relatively small amounts of the conjugated diene are reacted with the intermediate in the second step. The mole ratio of conjugated diene to 1-alkyne in the intermediate is at least about 2:1 and may be as high as 30:1. In one preferred embodiment, the mole ratio of conjugated diene to 1-alkyne is in a range of from about 8:1 to about 20:1.

The polymetalated compounds of this invention contain active as well as inactive metal. The presence of at least two different types of carbon metal linkages in the compositions of this invention can be shown by both chemical and physical evidence. Gilman titration with allyl bromide distinguishes between metal acetylide (—C≡C—M) which is inactive and other carbon lithium linkages (—C—C—M) which are active, *J. Organometal Chem.*, 1 (1963) 8. Titration of the compositions of this invention show 50%, 67% and 75% of the total carbon-metal linkages are "active" corresponding to di-, tri-, and tetra-metalated alkynes. Ultraviolet and visible spectral studies show peak absorbances at 300–340 NM and 400–450 NM for the compositions of this invention corresponding to inactive and active metal linkages, respectively.

An important property of these compositions is that they are soluble in hydrocarbon solvents, and the solutions are stable at room temperature for an extended period of time. The terms "soluble in hydrocarbon solvent" or "hydrocarbon soluble" as used in the specifications and claims indicate that the materials are soluble in hydrocarbons to the extent of at least about 5 per 100 g of solvent, particularly an aliphatic solvent such as hexane, at temperatures of about 25° C. The compositions are useful as catalysts in the anionic polymerization and copolymerization of various hydrocarbon monomers.

The following examples illustrate the preparation of the intermediates and the hydrocarbon soluble polymetalated 1-alkyne compositions of the present invention. Unless otherwise indicated, all parts and percentages are by weight, temperatures are in degrees centigrade and pressure is at or near atmospheric pressure.

PREPARATION OF INTERMEDIATES

EXAMPLE A

To a solution of 2 ml. (13.56 mM) of 1-octyne in 30 ml. of hexane in a 7-ounce beverage bottle equipped with rubber liner, 3-hole crown cap and magnetic stirrer is charged 9 ml. (13.56 mM, 1.5M solution) of n-butyllithium in hexane through a disposable syringe at room temperature under nitrogen. The monolithium salt was precipitated immediately as a white solid. Additional n-butyllithium solution in hexane (9 ml., 13.56 mM, 1.5M solution) is added to the bottle and the mixture is stirred magnetically at room temperature to form a pale yellow solution and a yellow solid precipitate. Titration of the yellow solid utilizing the procedure described by H. Gilman indicates 50.6% active carbon-lithium linkage. The calculated active carbon-lithium linkage for this product is 50%.

EXAMPLE B

To a solution of 1-octyne (0.55 ml., 3.73 mM) in 20 ml. of hexane, n-butyllithium (7 ml., 11.2 mM, 1.6M solution) is added slowly through a disposable syringe at room temperature under nitrogen. After the addition is complete, the resulting pale lemon solution containing a small amount of precipitate is vigorously shaken, and then the mixture is allowed to stand at room temperature for five hours. Titration of the solid product by the Gilman technique indicates that 96–98% of the theoretical carbon-lithium linkages are obtained.

PREPARATION OF DIENE-MODIFIED POLYMETALATED 1-ALKYNES

EXAMPLE 1

To a solution of 1-octyne (0.8 ml., 5.42 mM, 98% purity) in 20 ml. of dry hexane in a 7-ounce beverage bottle equipped with rubber liner and three-hole crown cap are charged 7 ml. of n-butyllithium (10.85 mM, 1.55M solution) through a disposable syringe at room temperature under nitrogen. The resulting slurry is shaken vigorously to complete the reaction. The resulting pale yellow solution is allowed to stand at room temperature for about one hour. To the solution is charged 25 gms. of 1,3-butadiene in hexane (24.2% butadiene, 112 mM butadiene). The mixture is tumbled in a bath maintained at about 80° C. for three hours. The resulting reddish brown solution is cooled at room temperature. Analysis of the solution by Gilman's titration technique indicates 48.9% active carbon-lithium linkages. The calculated active carbon-lithium linkage for 1,3-dilithio-1-octyne is 50.0%.

EXAMPLE 2

To a solution of 0.55 ml. of 1-octyne (3.73 mM) in dry hexane contained in a 7-ounce bottle equipped with rubber liner and three-hole crown cap are charged 7 ml. of n-butyllithium (11.2 mM, 1.6M solution) through a disposable syringe at room temperature under nitrogen. The resulting slurry is shaken vigorously to complete the reaction, and the resulting pale yellow solution is allowed to stand at room temperature for one hour. To this solution is charged 25 gms. of 1,3-butadiene in hexane (24.2% butadiene, 112 mM butadiene). The mixture is tumbled in a bath heated to about 80° C. for three hours, and the resulting reddish brown solution is cooled and stored. Analysis of the solution obtained in this manner indicates active carbon-lithium linkage of 63.6%. The calculated active carbon lithium linkage for 1,3,3-trilitho-octyne is 66.7%.

EXAMPLE 3

To a 1500 ml. glass reactor equipped with thermometer, stirrer, heating means, pressure means, inlet and outlet ports are charged 150 gms. of dry hexane, 217 gms. (498 mM) of n-butyllithium (1.54M) in hexane, and a solution of 18 gms. (166.3 mM) of 1-octyne in 30 gms. of dry hexane. The reaction mixture is maintained under a nitrogen atmosphere as the n-butyllithium and 1-octyne are added to the reactor. After the above ingredients are added to the reactor, the mixture is stirred at room temperature for 30 minutes under nitrogen, and 360 gms. of a 1,3-butadiene/hexane blend containing 87.5 gms. of 1,3-butadiene are added to the reactor. This mixture is stirred at 80° C. for 150 minutes whereupon a homogeneous red solution is obtained. This solution is allowed to cool to room temperature and transferred to storage bottles under a nitrogen atmosphere. Gilman's titration indicates the presence of 62.18% active carbon-lithium linkages at 0.2708 molarity. The calculated carbon-lithium linkage is 66.7%.

Two-hundred grams of the catalyst solution is coagulated with excess methanol in the presence of an antioxidant (e.g., 1% di-tertiary-butyl-para cresol). The resulting oily product is dried at 50° C. under vacuum. Gel permeation chromatography analysis of the product indicates a 1123 Mw.

EXAMPLES 4–6

The general procedure of Example 2 is repeated utilizing different 1-alkynes as summarized in Table I. The reaction conditions and the analysis of the resulting products also are summarized in Table I.

TABLE I

| Example | 4 | 5 | 6 |
| --- | --- | --- | --- |
| 1-alkyne | 1-hexyne | 1-nonyne | 1-dodecyne |
| Hexane (ml.) | 20 | 20 | 20 |
| 1-alkyne (mM) | 3.73 | 3.73 | 3.73 |
| n-BuLi (nM) | 11.20 | 11.20 | 11.20 |
| Bd-Hexane* (g) | 25 | 25 | 25 |
| Temp. (°C.) | 80 | 80 | 80 |
| Time (hrs.) | 3 | 3 | 3 |
| Product Color | | reddish brown | |
| % Active C—Li bond** | 59.5 | 60.0 | 59.3 |

*blend contains 24.2% Bd.
**determined by Gilman titration.

The polymetalated 1-alkynes of the present invention are stable for an extended period of time at room temperature. For example, the polymetalated compositions can be stored at room temperature under a nitrogen atmosphere for up to six months or more without significant loss of their activity as catalysts for anionic polymerization reactions.

The polymetalated 1-alkyne compositions of the present invention are useful as catalyts for the anionic polymerization of a variety of hydrocarbon monomers including olefins such as ethylene, styrene, α-methylstyrene, divinylbenzene and vinyl toluene; and dienes such as butadiene, isoprene, piperylene and 2,3-dimethylbutadiene. The catalysts also may be utilized for preparing copolymers or mixtures containing two or more of the above olefins, dienes, or mixtures thereof. The polymers and copolymers obtained in this manner contain alkali metal, and polymers of these types have been referred to as "living polymers". The "live ends" of the polymers (i.e., the carbon-alkali metal bonds) can be used to couple the polymers or to introduce terminal, functional groups such as silane, hydroxyl, carboxyl, mercapto, amino, etc. by procedures well known to those skilled in the art.

While the present invention has been described in connection with certain specific embodiments, it will be appreciated that modifications of the disclosed invention will be suggested to those skilled in the art upon reading this disclosure. Therefore, it is to be understood that the invention disclosed herein is intended to cover such modifications as fall within the scope of the appended claims.

I claim:

1. A hydrocarbon soluble polymetalated 1-alkyne composition characterized by the formula

(I)

wherein R is hydrogen, a hydrocarbyl group or $R^1M$, M is an alkali metal, and each $R^1$ is independently a divalent oligomeric hydrocarbyl group comprising moieties derived from a 1,3-conjugated diene, and wherein the total number moieties derived from a conjugated diene in all of the $R^1$ groups in Formula I is from about 2 to about 30.

2. The composition of claim 1 wherein the alkali metal is lithium.

3. The composition of claim 1 wherein R is an alkyl group containing from 1 to 15 carbon atoms.

4. The composition of claim 1 wherein the conjugated diene is an alkadiene containing from 4 to about 12 carbon atoms.

5. The composition of claim 4 wherein the diene is 1,3-butadiene, isoprene or piperylene.

6. The composition of claim 1 wherein the total number of conjugated diene derived moieties in all of the R groups is from about 8 to about 20.

7. The composition of claim 1 characterized by the formula $$(C_5H_{11})-\underset{\underset{(C_4H_6)_yLi}{|}}{\overset{\overset{(C_4H_6)_xLi}{|}}{C}}-C\equiv C-Li$$

wherein x and y are each independently at least 1 and their sum (x+y) is from about 3 to about 30.

8. The composition of claim 1 characterized by the formula $$Li(C_4H_6)_z-\underset{\underset{(C_4H_6)_yLi}{|}}{\overset{\overset{(C_4H_6)_xLi}{|}}{C}}-C\equiv C-Li$$

wherein x, y and z are each independently at least 1 and their sum (x+y+z) is from 3 to about 30.

9. A hydrocarbon soluble polymetalated 1-alkyne catalyst for anionic polymerizations comprising the reaction product of a 1-alkyne, an organometallic compound R°M, and a 1,3-conjugated diene wherein R° is a hydrocarbyl group, M is an alkali metal, the mole ratio of conjugated diene to 1-alkyne is at least about 2:1, and the reaction is conducted at a temperature of at least about 70° C.

10. The catalyst of claim 9 wherein the mole ratio of organometallic compound to 1-alkyne is about 2:1 to about 4:1.

11. The catalyst of claim 9 wherein the mole ratio of conjugated diene to 1-alkyne is from about 8 to about 20.

12. The catalyst of claim 9 wherein the alkali metal M is lithium.

13. The catalyst of claim 9 wherein the 1-alkyne is characterized by the formula $$R(R^3)C(H)-C\equiv CH \qquad (II)$$

wherein R and $R^3$ are each independently hydrogen or an alkyl group.

14. The catalyst of claim 13 wherein R is an alkyl group containing from 1 to about 15 carbon atoms and $R^3$ is hydrogen.

15. The catalyst of claim 13 wherein R is an alkyl group containing from 1 to about 6 carbon atoms and $R^3$ is hydrogen.

16. The catalyst of claim 13 wherein R and $R^3$ are hydrogen.

17. The catalyst of claim 9 wherein R° is an alkyl group containing from 1 to 10 carbon atoms.

18. The catalyst of claim 9 where the conjugated diene is an aliphatic, 1,3-diene.

19. The catalyst of claim 18 wherein the conjugated diene is 1,3-butadiene, isoprene or piperylene.

20. The catalyst of claim 9 wherein the reaction is conducted at a temperature in the range of about 70° C. to about 150° C.

21. The catalyst of claim 9 wherein the reaction is conducted at a temperature of from about 70° C. to about 100° C.

22. A hydrocarbon soluble polylithiated 1-alkyne catalyst for anionic polymerizations comprising a reaction product of a 1-alkyne, an alkyl lithium compound containing from about three to about 10 carbon atoms in the alkyl group, and a 1,3-conjugated alkadiene wherein the mole ratio of lithium compound to 1-alkyne is about 2:1 to about 4:1, the mole ratio of conjugated alkadiene to 1-alkyne is from about 8:1 to about 20:1, the 1-alkyne is characterized by the formula $$RCH_2-C\equiv CH \qquad (III)$$

wherein R is hydrogen or an aliphatic group containing from 1 to about 6 carbon atoms, and the reaction is conducted at a temperature of from about 70° C. to about 150° C.

23. The catalyst of claim 22 wherein the 1-alkyne is 1-octyne.

24. The catalyst of claim 22 wherein the 1-alkyne is propyne.

25. The catalyst of claim 22 wherein the alkyl lithium compound is n-butyl lithium.

26. The catalyst of claim 22 wherein the conjugated alkadiene is 1,3-butadiene, isoprene or piperylene.

27. A method of preparing a hydrocarbon soluble polymetalated 1-alkyne catalyst for anionic polymerizations which comprises the steps of (a) reacting in a hydrocarbon solvent, a 1-alkyne with an organometallic compound R°M in a mole ratio of about 1:2 to about 1:4, wherein R° is a hydrocarbyl group and M is an alkali metal to form an intermediate, and (b) reacting said intermediate with a 1,3-conjugated diene at a temperature of at least about 70° C. wherein the mole ratio of conjugated diene to 1-alkyne is at least about 2:1.

28. The method of claim 27 wherein the mole ratio of conjugated diene to 1-alkyne is from about 8:1 to 20:1.

29. The method of claim 27 wherein the alkali metal M is lithium.

30. The method of claim 27 wherein the 1-alkyne is characterized by the formula $$R(R^3)C(H)-C\equiv CH \qquad (II)$$

wherein R and $R^3$ are each independently hydrogen or an alkyl group.

31. The method of claim 30 wherein R is an alkyl group containing from 1 to about 15 carbon atoms and $R^3$ is hydrogen.

32. The method of claim 30 wherein R is an alkyl group containing from 1 to about 6 carbon atoms and $R^3$ is hydrogen.

33. The method of claim 30 wherein R and $R^3$ are hydrogen.

34. The method of claim 27 wherein R° is an alkyl group containing from 1 to 10 carbon atoms.

35. The method of claim 27 where the conjugated diene is a 1,3-alkadiene.

36. The method of claim 35 wherein the conjugated diene is 1,3-butadiene, isoprene or piperylene.

37. A method of anionically polymerizing polymerizable monomers selected form the group consisting of olefins, dienes, and mixtures thereof which comprise contacting said monomers with the catalyst of claim 9.

* * * * *